United States Patent [19]

Knowles et al.

[11] 4,148,218
[45] Apr. 10, 1979

[54] APPARATUS FOR APPLYING TENSILE STRESS TO FIBER

[75] Inventors: Daniel H. Knowles, Painted Post; William E. Lock, Horseheads, both of N.Y.

[73] Assignee: Corning Glass Works, Corning, N.Y.

[21] Appl. No.: 897,193

[22] Filed: Apr. 17, 1978

[51] Int. Cl.² ............................................. G01L 5/04
[52] U.S. Cl. ..................................... 73/829; 65/11 W
[58] Field of Search ................. 73/95.5, 143; 65/11 R, 65/11 W

[56] References Cited

U.S. PATENT DOCUMENTS

| 3,650,717 | 3/1972 | Canfield | 65/11 W |
| 3,674,221 | 7/1972 | Riemersma | 73/95.5 X |

*Primary Examiner*—Jerry W. Myracle

*Attorney, Agent, or Firm*—William J. Simmons, Jr.; Walter S. Zebroski; Richard E. Kurtz

[57] ABSTRACT

First and second tractor assemblies apply a preset tension to incremental lengths of fiber which moves continuously through the apparatus. The apparatus performs the functions of fiber pulling and non-destructive testing of all of the fiber. Each tractor assembly includes a tractor wheel and belt wheels. A belt extends around the belt wheels and engages the tractor wheel in an arc. The fiber passes between the belt and the tractor wheel in this arc. The second tractor assembly has a constant torque drive with an unloaded speed which is faster than that of the first tractor assembly. The second tractor assembly pulls the fiber thereby reducing the speed by causing the constant torque device to overload and slip.

12 Claims, 7 Drawing Figures

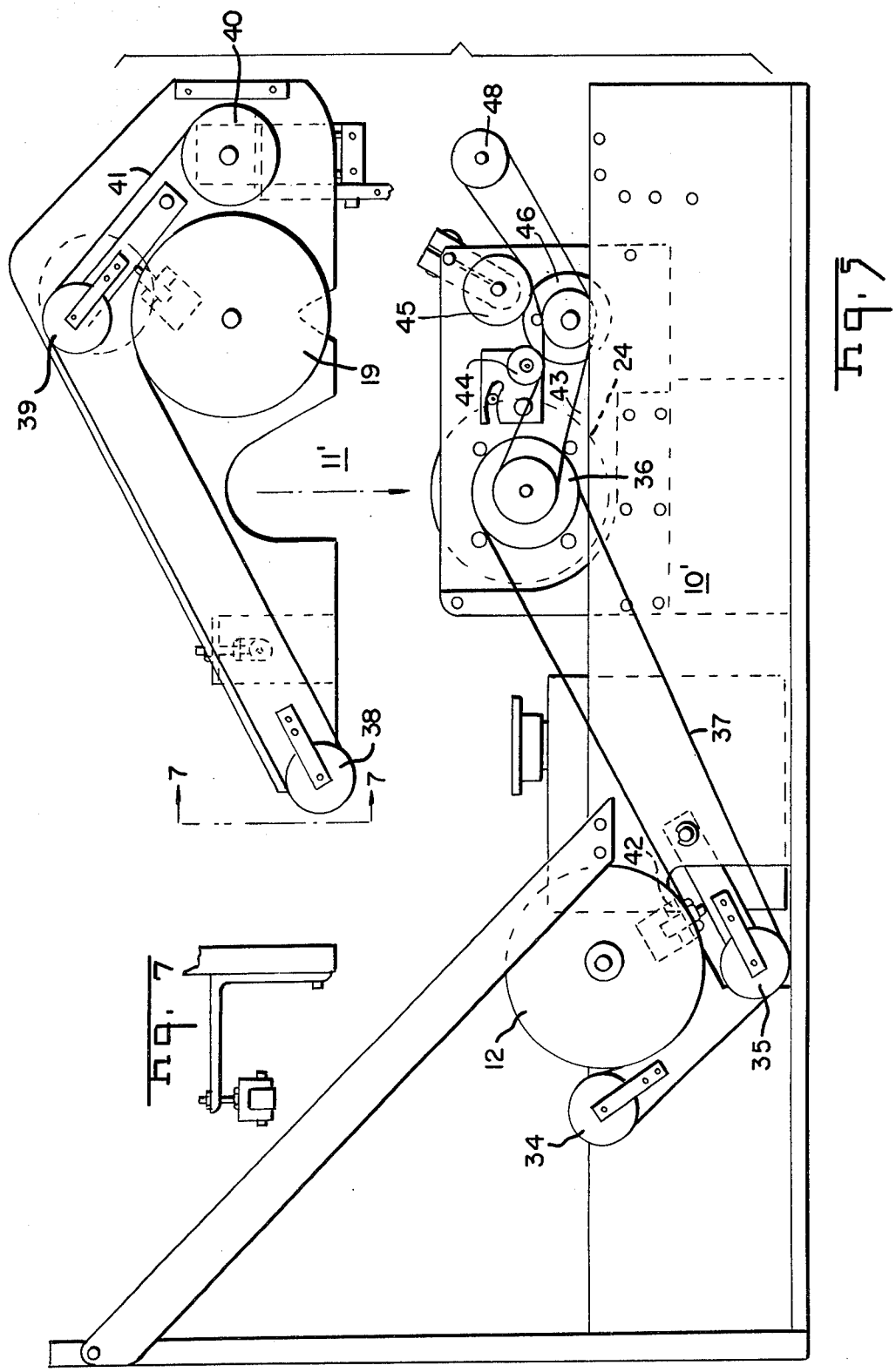

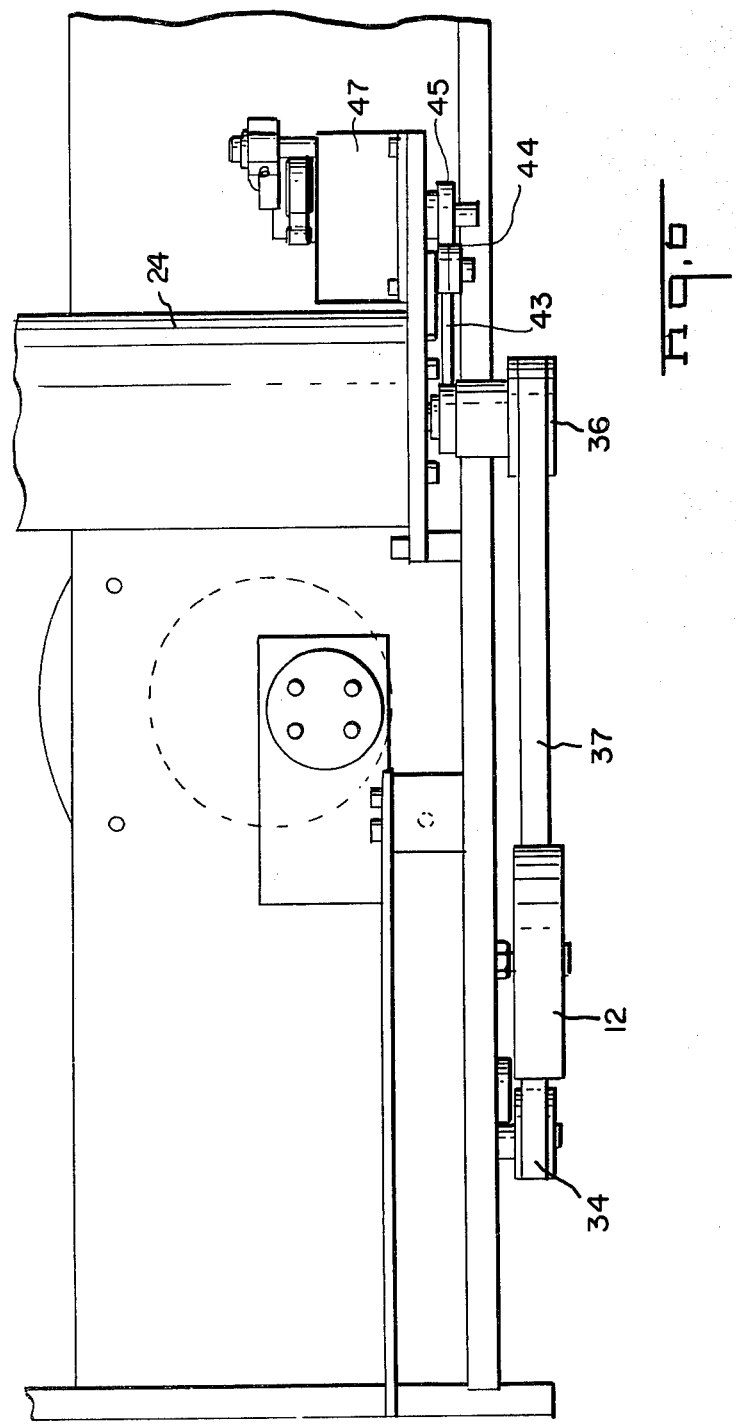

APPARATUS FOR APPLYING TENSILE STRESS TO FIBER

BACKGROUND OF THE INVENTION

This invention relates to apparatus for applying tensile stress to a fiber and more particularly to a machine for pulling and strength testing an optical waveguide.

The increased burden on communication systems has fostered the development of high capacity systems using optical waveguides. These optical waveguides are constructed of a transparent dielectric material such as glass. They consist of a central core surrounded by a cladding having an index of refraction less than the index of refraction of the core. Light propagates along the waveguide. Recently, optical waveguides having very low attenuation per unit length have been developed. For example, the Maurer et al U.S. Pat. No. 3,659,915, and Keck et al U.S. Pat. No. 3,711,262 describe an optical waveguide comprising a core and a cladding layer.

In the fabrication of optical waveguides, the waveguide is heated and drawn into its final form. Any imperfections in the surface of the waveguide can result in fracture of the waveguide during use. Waveguides must be tested by applying tension to detect these flaws. Prior art tensile testers use clamps which often abrade the surface of the waveguide, thereby causing flaws during the testing. Also, prior art tensile testers test the waveguide to destruction. Because of this, often only a small portion of the waveguide is actually tested.

SUMMARY OF THE INVENTION

In accordance with this invention, fibers such as optical waveguides are continuously tensile tested in apparatus which performs the functions of fiber pulling and strength testing of 100% of the fabricated fiber.

It is an object of the present invention to provide controlled tension in incremental lengths of a fiber which moves continuously through the apparatus of this invention.

It is another object of the present invention to provide a force on the fiber surface in a manner which does not abrade the surface.

It is another object of the present invention to apply tensile stress to a fiber to establish minimum strength values for all of the fabricated fiber.

It is another object of the present invention to provide an apparatus which is easy to thread.

It is another object of the present invention to provide variable speed traction of a fiber which is continuously pulled.

The foregoing and other objects, features and advantages of the invention will be better understood from the following more detailed description and appended claims.

DESCRIPTION OF THE DRAWINGS

FIG. 5 is a view similar to FIG. 4 but showing the upper tractor assembly in exploded condition;
and
FIG. 6 is a top plan view of the lower tractor assembly.

DESCRIPTION OF THE PREFERRED EMBODIMENT

Figure 1:
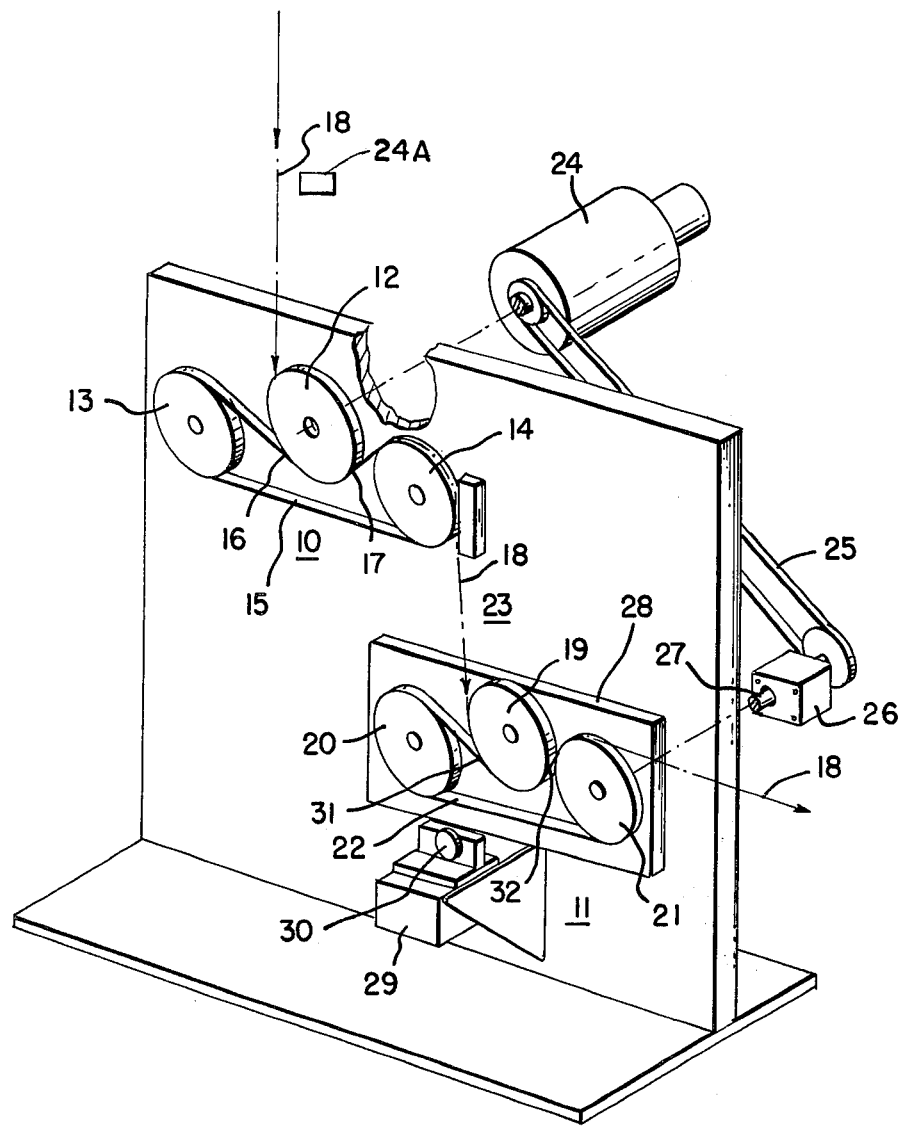
FIG. 1 depicts the apparatus of the present invention.

Referring to FIG. 1 the apparatus includes a first tractor assembly 10 and a second tractor assembly 11. The tractor assembly 10 includes tractor wheel 12 and belt wheels 13 and 14 on both sides of tractor wheel 12. A belt 15 extends around the two belt wheels and engages tractor wheel 12 in an arc between 16 and 17. A fiber 18, such as an optical waveguide, is clamped between the belt and tractor wheel 12 throughout this arc. As used herein the "tractor wheel" is the wheel which clamps the fiber against the belt to apply tension to the fiber. The tractor wheel can be either a driven or an idler wheel.

The second tractor assembly 11 is similar to the first. It includes a tractor wheel 19, belt wheels 20 and 21 and a belt 22.

The fiber 18 is introduced into the junction between belt 15 and tractor wheel 12 at the point 16. Rotation of the belt 15 and tractor wheel 12 causes a point on the fiber to be transported through the arc. The fiber passes through the first tractor assembly 10, through an open space 23 and then through the second tractor assembly 11.

The first tractor assembly is driven by variable speed drive motor 24. A belt 25 extends to the constant torque device 26 which provides means for driving the second tractor assembly. Constant torque device 26 includes a clutch and a drive including a shaft 27 connected to the belt wheel 21. The unloaded speed of this drive is faster than the rotational speed of the first tractor assembly. When the second tractor assembly pulls the fiber, its speed is reduced by causing the constant torque device 26 to overload and the clutch to slip.

The belt wheels and tractor wheel of the second tractor assembly 11 are mounted on a plate 28. This assembly is pivoted around the belt wheel shaft 27. A load cell 29 supports the second tractor assembly 11 at the free end thereof. The load cell includes a transducer 30 which produces an output indicating the force thereon. The fiber tension is applied at a right angle to the support for the tractor assembly. Therefore, the output of the load cell 29 indicates applied tension in the fiber. When tension is increased, less force is applied to transducer 30 and vice versa.

Drive motor 24 is a servo motor connected in a servo loop with the output of diameter sensing device 24A. The speed of motor 24 is controlled to produce a uniform diameter fiber which is drawn from a furnace. If a fiber diameter larger than nominal is sensed, motor 24 speeds up; if the diameter is below the nominal diameter, the motor is slowed. Constant tension is applied to the fiber at all speeds.

Fiber tension increases as the fiber passes through the arc between the points 16 and 17. As it leaves the arc at the point 17 the tension is at the test setting. Tension at this test setting is applied to the fiber as it passes through the open space 23. Tension is decreased as the fiber passes through the arc between the points 31 and 32 on the second tractor wheel. In this manner, a constant test tension is applied to the fiber in the incremental length between the point 17 and the point 31. Then tension is released.

The embodiment shown in FIG. 1 facilitates easy threading because the leading end of the fiber falls directly from the first tractor assembly 10 into the junction at 31 of the belt and second tractor wheel 19. An air jet may be provided to guide the fiber during loading.

If the fiber slides over the friction surfaces, the fiber surfaces will be abraded resulting in considerable loss of strength. If the fiber is pressed between the belt and tractor wheel, it can be crushed by excessive force. It is important to obtain as much friction between the tractor wheel and the fiber as possible without applying excessive force to the fiber. Typically, the coefficient of friction for plastic coated fiber and various tractor wheels is between 0.15 and 0.5. In accordance with this invention, the friction between the fiber and the tractor wheel is increased without applying excessive force to the fiber given the available coefficients.

Figure 2:
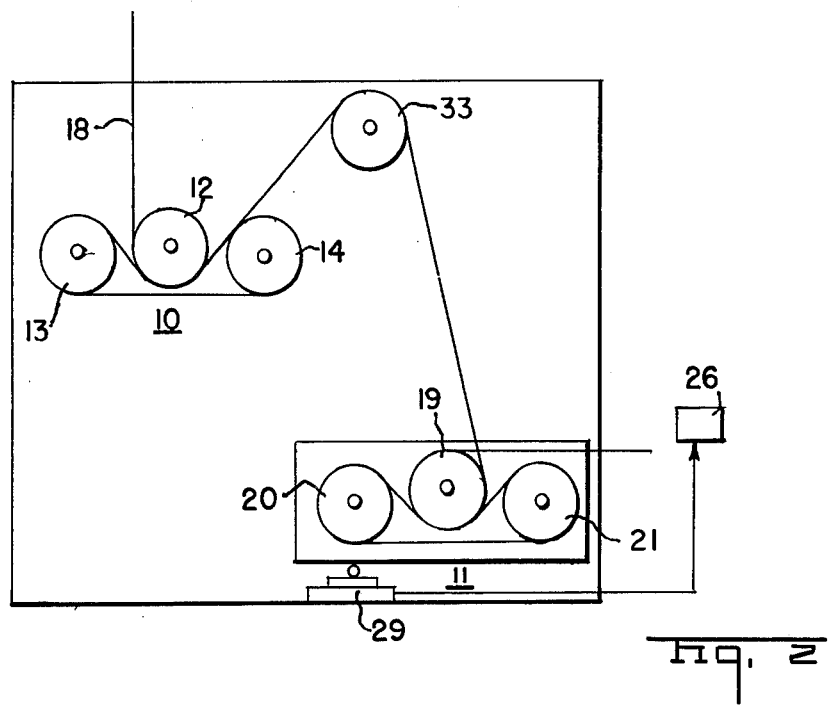
FIG. 2 shows a modification of the invention.

Referring to FIG. 2, an idler wheel 33 pulls the fiber away from the belt 15 so that the fiber does not wrap around belt wheel 14. The belt stretches at its outside surface as it passes around a wheel. It has been found that if the fiber is in contact with this stretching surface, fiber breakage results. Provision of the idler wheel 33 in the position shown obviates this breakage. FIG. 2 also depicts a feature by which the friction between the fiber and the tractor wheel is increased by wrapping the fiber around the tractor wheel 19.

FIG. 2 shows a modification of the invention in which the output of load cell 29 is connected to control the constant torque device 26. By modifying the power output of the clutch in accordance with the output of the load cell 29, the tension in the fiber can be closely controlled.

Figure 3:
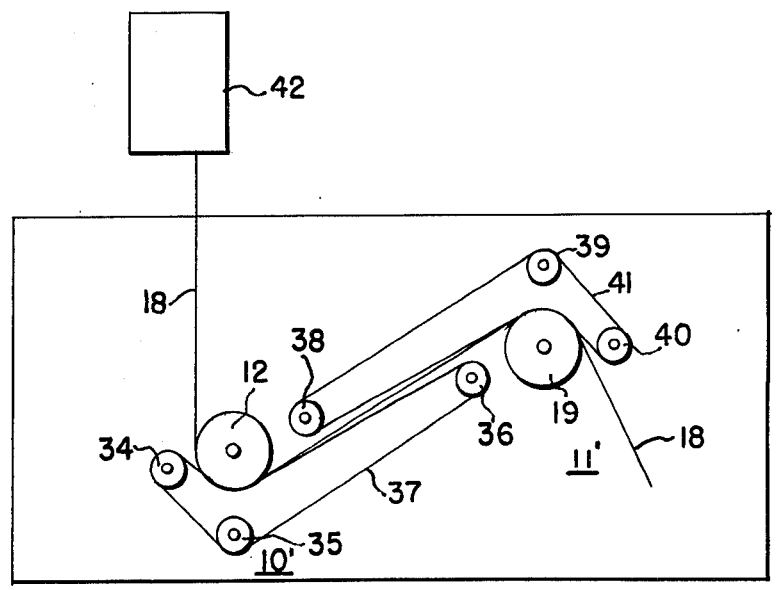
FIG. 3 shows the preferred embodiment of the invention.

FIG. 3 depicts a preferred embodiment of the invention. In this embodiment, the first tractor assembly 10' includes belt wheels 34–36. These belt wheels are positioned around the tractor wheel 12 so that the belt 37 engages tractor wheel 12 throughout approximately 120° of arc. Second tractor assembly 11' includes tractor wheel 19 and belt wheels 38–40 positioned around it. Again, the belt 41 engages tractor wheel 19 throughout approximately 120° of arc.

Belt wheels 36 and 38 are arranged so that belts 37 and 41 define a path between the first and second tractor assemblies. This facilitates threading because the path guides the fiber between the first and second assemblies. Also, the wheels are arranged so that the fiber is out of contact with the belt from the point it leaves the wheel 12 to the point it engages wheel 19.

FIG. 3 shows the apparatus of this invention pulling fiber as it exits from the furnace 42. As more fully explained in the Keck et al patent previously referred to, optical waveguides are fabricated by heating them in a furnace and drawing them by applying tension thereto. The apparatus of this invention performs this drawing function while at the same time testing the waveguide by applying a controlled tension thereto. Furthermore, this testing is performed on all of the fiber as it is fabricated, rather than destructively testing segments of the fiber as was previously done. Alternatively, the apparatus of the present invention can be used to apply de-reeling tension to waveguide fiber which has already been drawn and wound on a reel. The apparatus of the present invention is capable of applying tension up to 100,000 psi on 140 micron diameter fibers.

Figure 4:
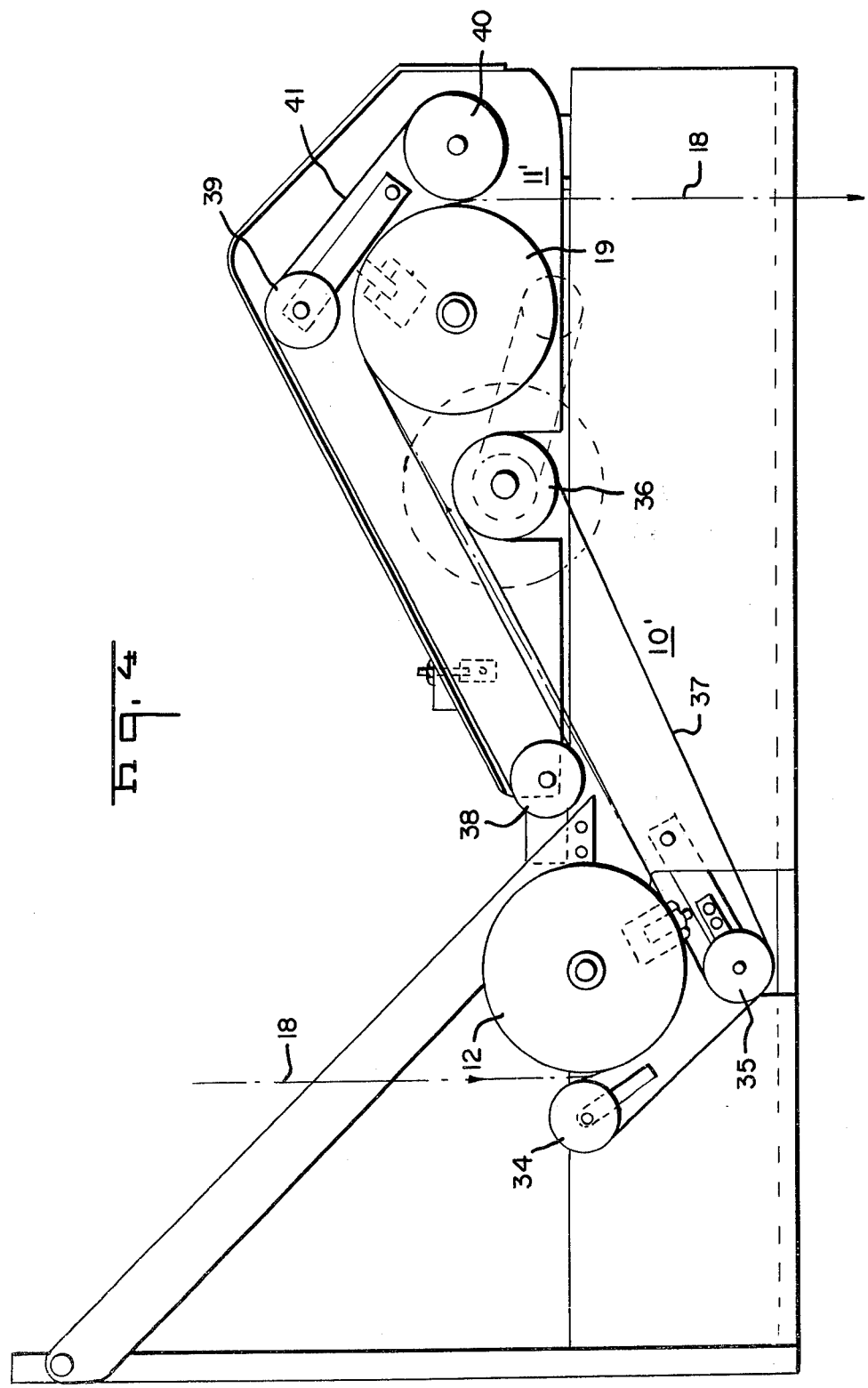
FIG. 4 is a front elevation view of the mechanism of FIG. 3 showing both upper and lower tractor assemblies in their related positions.

The preferred embodiment of the invention is shown in more detail in FIGS. 4–6. Like reference numerals are used to denote like parts. Motor 24 drives the belt wheel 36 of the first tractor assembly. Belt tightener 42 can be adjusted to provide the desired tension in the belt 37.

A belt 43 connects belt wheel 36 with the second tractor assembly. The belt 43 contacts the wheels 44–46 of the drive assembly 47 which includes the clutch. The pulley 48 has a shaft connected to the belt wheel 40. This preferred embodiment of the invention has the advantage of very low inertia which allows a fast change in speed in response to sensed changes in fiber diameter. Also, this preferred embodiment of the invention has low friction in the rotating components resulting in more accurate measurement of tension.

Various modifications may be made. A constant speed motor may be substituted for the variable speed motor 24. A torque motor may be substituted for the clutch and drive which makes up the constant torque device 26. Other modifications are within the true spirit and scope of this invention. The appended claims are, therefore, intended to cover all such modifications.

While a particular embodiment of the invention has been shown and described, various modifications will occur to those skilled in the art. The appended claims are, therefore, intended to cover all such modifications which fall within the true spirit and scope of the invention.

What is claimed is:

1. Apparatus for applying tension to incremental lengths of a fiber comprising:
   a first tractor assembly including at least one wheel,
   means for driving said first assembly,
   holding means for clamping said fiber against said wheel throughout an arc thereof,
   a second tractor assembly including at least one wheel,
   second holding means for clamping said fiber against said last-named wheel throughout an arc thereof, and
   constant torque drive means for driving said second tractor assembly to apply tension to said fiber between the end of said arc on one wheel and the beginning of said arc on the other wheel.

2. The apparatus recited in claim 1 further comprising a load cell for measuring said tension.

3. The apparatus recited in claim 1 wherein said first and second holding means include a belt and a tractor wheel, said fiber being held therebetween.

4. The apparatus recited in claim 3 wherein each tractor assembly includes belt wheels disposed on both sides of a tractor wheel, said belts extending around said belt wheels and engaging said tractor wheel throughout an arc thereof.

5. The apparatus recited in claim 4 wherein said second tractor assembly is pivoted at one end thereof, and
   a force transducer at the other end of said second assembly producing an output indicating the tension in said fiber.

6. The apparatus recited in claim 4 wherein a tractor assembly includes three belt wheels engaging a belt, two of said belt wheels being positioned to increase the arc through which said belt engages one of said tractor wheels.

7. The apparatus recited in claim 4 further comprising an idler wheel in the path of said fiber between said first and second tractor assemblies, said idler wheel being positioned to move said fiber out of contact with said belts.

8. The apparatus recited in claim 3 wherein each tractor assembly includes three belt wheels and a belt extending around said belt wheels, said belt engaging said tractor wheel throughout an arc thereof, said belt wheels being disposed around said tractor wheel to move said fiber out of contact with said belts.

9. The apparatus recited in claim 8 wherein the belts define a path between said first and second tractor assemblies to facilitate threading of said fiber.

10. The apparatus recited in claim 1 further comprising a load cell producing an output indicating said tension, said output being applied to control said constant torque drive means.

11. The apparatus recited in claim 1 wherein said means for driving said first assembly is a variable speed servo motor, and a diameter sensing transducer having its output connected to control the speed of said variable speed servo motor.

12. The apparatus recited in claim 11 in combination with a furnace, said motor drawing said fiber from said furnace at a speed which controls the diameter of said fiber.